(12) United States Patent
Christakis et al.

(10) Patent No.: US 10,537,450 B2
(45) Date of Patent: Jan. 21, 2020

(54) METHOD FOR LOADING A STENT INTO A DELIVERY DEVICE

(71) Applicant: BOSTON SCIENTIFIC SCIMED, INC., Maple Grove, MN (US)

(72) Inventors: Laura E. Christakis, Boston, MA (US); Colby Harris, Weston, MA (US); Stan R. Gilbert, Litchfield, NH (US); Gerald Fredrickson, Westford, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 112 days.

(21) Appl. No.: 15/852,574

(22) Filed: Dec. 22, 2017

(65) Prior Publication Data
US 2018/0185183 A1    Jul. 5, 2018

Related U.S. Application Data

(60) Provisional application No. 62/440,239, filed on Dec. 29, 2016.

(51) Int. Cl.
*A61F 2/962* (2013.01)
*B23P 11/00* (2006.01)
*A61F 2/95* (2013.01)

(52) U.S. Cl.
CPC .............. *A61F 2/95* (2013.01); *A61F 2/962* (2013.01); *A61F 2002/9522* (2013.01); *B23P 11/005* (2013.01)

(58) Field of Classification Search
CPC .......... B23P 11/00; B23P 11/005; A61F 2/962; A61F 2002/9522; A61F 2250/0039
See application file for complete search history.

(56) References Cited

U.S. PATENT DOCUMENTS

| | | |
|---|---|---|
| 5,672,169 A | 9/1997 | Verbeek |
| 5,893,852 A | 4/1999 | Morales |

(Continued)

FOREIGN PATENT DOCUMENTS

| | | |
|---|---|---|
| EP | 2742917 A1 | 6/2014 |
| WO | 0121103 A2 | 3/2001 |
| WO | 2013177684 A1 | 12/2013 |

OTHER PUBLICATIONS

International Search Report and Written Opinion dated Mar. 7, 2018 for International Application No. PCT/US2017/068194 (10 pgs).

*Primary Examiner* — Christopher J Besler
(74) *Attorney, Agent, or Firm* — Seager, Tufte & Wickhem, LLP

(57) ABSTRACT

A method of loading an expandable stent into a delivery device may include positioning a middle portion of the expandable stent in a collapsing fixture including a passage extending therethrough, radially compressing the middle portion of the expandable stent in the passage before any other portion of the expandable stent while a first end of the expandable stent is disposed outside of the passage, moving the collapsing fixture relative to the expandable stent, radially compressing the expandable stent from the middle portion toward the first end of the expandable stent, and inserting the first end of the expandable stent followed by the middle portion of the expandable stent into a distal end of an elongate outer sheath of the delivery device.

16 Claims, 18 Drawing Sheets

(56) References Cited

U.S. PATENT DOCUMENTS

| | | | |
|---|---|---|---|
| 5,893,867 | A | 4/1999 | Bagaoisan et al. |
| 5,947,993 | A | 9/1999 | Morales |
| 5,951,540 | A | 9/1999 | Verbeek |
| 6,090,035 | A | 7/2000 | Campbell et al. |
| 6,096,027 | A | 8/2000 | Layne |
| 6,132,458 | A | 10/2000 | Staehle et al. |
| 6,364,870 | B1 | 4/2002 | Pinchasik |
| 6,618,921 | B1 | 9/2003 | Thornton |
| 8,308,792 | B2 | 11/2012 | Ellsworth et al. |
| 8,474,122 | B2 | 7/2013 | Melsheimer |
| 9,364,324 | B2 | 6/2016 | Rafiee et al. |
| 2003/0083730 | A1 | 5/2003 | Stinson |
| 2005/0234537 | A1 | 10/2005 | Edin |
| 2009/0192601 | A1* | 7/2009 | Rafiee .................. A61F 2/2436 623/2.11 |
| 2010/0121424 | A1* | 5/2010 | Kubena .................. A61F 2/95 623/1.11 |
| 2014/0165365 | A1 | 6/2014 | Fargahi |
| 2015/0040949 | A1* | 2/2015 | Zucker .................. A61F 2/0095 134/22.11 |
| 2016/0022456 | A1 | 1/2016 | Butler et al. |
| 2016/0228251 | A1 | 8/2016 | Nyuli et al. |

* cited by examiner

METHOD FOR LOADING A STENT INTO A DELIVERY DEVICE

CROSS-REFERENCE TO RELATED APPLICATIONS

This application claims priority to U.S. Provisional Application Ser. No. 62/440,239, filed Dec. 29, 2016, the entirety of which is incorporated herein by reference.

TECHNICAL FIELD

The present disclosure pertains to methods for assembling a stent delivery system, as well as to stent delivery assemblies and devices. This invention also relates to a method for loading a stent into a stent delivery system.

BACKGROUND

A wide variety of intracorporeal medical devices have been developed for medical use, for example, intravascular use. Some of these devices include guidewires, stents, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

In a first aspect, a method of loading an expandable stent into a delivery device may comprise radially compressing a middle portion of the expandable stent before any other portion of the expandable stent, radially compressing the expandable stent from the middle portion toward a first end of the expandable stent, and thereafter, inserting the first end of the expandable stent followed by the middle portion of the expandable stent into a distal end of an elongate outer sheath of the delivery device.

In addition or alternatively, and in a second aspect, radially compressing the middle portion of the expandable stent includes positioning the middle portion of the expandable stent within a passage extending through a collapsing fixture with the first end positioned outside of the passage.

In addition or alternatively, and in a third aspect, the collapsing fixture has an open configuration and a closed configuration.

In addition or alternatively, and in a fourth aspect, the collapsing fixture includes an outer ring and a plurality of movable elements operatively connected thereto, the plurality of movable elements being configured to move radially inward relative to the outer ring to radially compress the expandable stent in the closed configuration.

In addition or alternatively, and in a fifth aspect, each of the plurality of movable elements includes a rolling element proximate the outer ring in the open configuration.

In addition or alternatively, and in a sixth aspect, each rolling element includes a concave profile configured to contact the expandable stent in the closed configuration.

In addition or alternatively, and in a seventh aspect, when the expandable stent is disposed within the collapsing fixture in the open configuration, each rolling element is spaced apart from the expandable stent.

In addition or alternatively, and in an eighth aspect, the collapsing fixture includes a first block portion configured to engage a second block portion in the closed configuration, the first block portion and the second block portion cooperating to at least partially define the passage, and a clamping portion configured to retain the first block portion in engagement with the second block portion when the collapsing fixture is in the closed configuration.

In addition or alternatively, and in a ninth aspect, the first block portion and the second block portion each include a tapered portion and a channel portion in communication with the tapered portion. The channel portion of the first block portion cooperates with the channel portion of the second block portion to form a reduced diameter portion of the passage configured to radially compress a portion of the expandable stent disposed therein.

In addition or alternatively, and in a tenth aspect, positioning the middle portion of the expandable stent within the passage includes positioning the middle portion of the expandable stent in the channel portion of the first block portion and then engaging the second block portion with the first block portion.

In addition or alternatively, and in an eleventh aspect, the collapsing fixture includes an annular collar at least partially defining the passage, the annular collar including a sleeve portion attached thereto. The sleeve portion is extendable from the annular collar toward the first end of the expandable stent after positioning the middle portion of the expandable stent within the passage to radially collapse the expandable stent into the constrained configuration from the middle portion toward the first end.

In addition or alternatively, and in a twelfth aspect, the sleeve portion includes an enlarged end opposite the annular collar, the enlarged end being configured to accept the distal end of the elongate outer sheath therein.

In addition or alternatively, and in a thirteenth aspect, the sleeve portion is a rolled material and radially compressing the expandable stent from the middle portion toward the first end of the expandable stent includes unrolling the sleeve portion toward the first end.

In addition or alternatively, and in a fourteenth aspect, the annular collar further includes a second sleeve portion attached thereto, the second sleeve portion being extendable from the annular collar toward a second end of the expandable stent opposite the first end after positioning the middle portion of the expandable stent within the passage to radially collapse the expandable stent into the constrained configuration from the middle portion toward the second end.

In addition or alternatively, and in a fifteenth aspect, positioning the middle portion of the expandable stent in the collapsing fixture occurs when the collapsing fixture is in the open configuration.

In addition or alternatively, and in a sixteenth aspect, the delivery device includes an inner shaft slidably disposed within the elongate outer sheath, and the inner shaft is disposed through a lumen of the expandable stent before the middle portion of the expandable stent is radially compressed.

In addition or alternatively, and in a seventeenth aspect, a method of loading an expandable stent into a delivery device may comprise radially collapsing a middle portion of an expandable stent in a passage of a collapsing fixture while a first end of the expandable stent is disposed outside of the passage, such that the middle portion of the expandable stent is collapsed before the first end of the expandable stent; thereafter, moving the collapsing fixture relative to the expandable stent such that the first end of the expandable stent is radially collapsed within the passage to a constrained configuration; and advancing the first end of the expandable stent into a distal end of an elongate outer sheath while at least a portion of the expandable stent is disposed within the collapsing fixture.

In addition or alternatively, and in an eighteenth aspect, a method of loading an expandable stent into a delivery device may comprise positioning the expandable stent in a collapsing fixture including a passage extending therethrough, wherein a middle portion of the expandable stent is disposed within the passage and a first end of the expandable stent is disposed outside of the passage; shifting the collapsing fixture from an open configuration to a closed configuration with the expandable stent positioned therein, thereby collapsing the middle portion of the expandable stent before any other portion of the expandable stent; thereafter, moving the collapsing fixture relative to the expandable stent such that the passage is moved from the middle portion of the expandable stent toward the first end of the expandable stent, thereby collapsing the first end of the expandable stent to a constrained configuration; and advancing the first end of the expandable stent into a distal end of an elongate outer sheath while at least a portion of the expandable stent is disposed within the collapsing fixture.

In addition or alternatively, and in a nineteenth aspect, the method may further comprise maintaining the expandable stent in a fixed position and moving the collapsing fixture axially away from the first end of the expandable stent as the first end of the expandable stent is advanced into the distal end of the elongate outer sheath.

In addition or alternatively, and in a twentieth aspect, in an expanded configuration of the expandable stent, the first end of the expandable stent has a greater outer diameter than the middle portion of the expandable stent.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
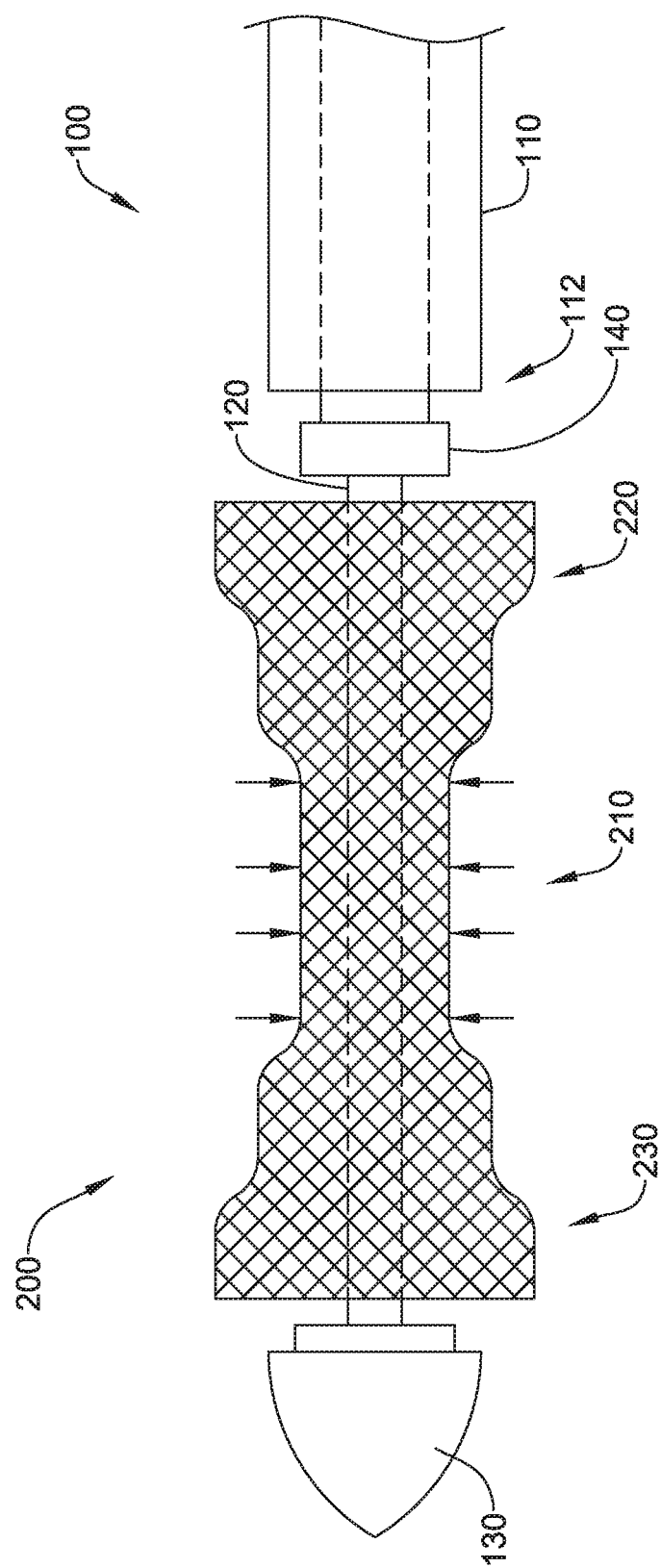
FIGS. 1-4 illustrate an example method of loading a stent into a delivery device.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a measurement of a stated or identified dimension or feature. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, a maximum "extent" may be considered a greatest possible dimension measured according to the intended usage. In some instances, a "minimum" extent may refer to a smallest possible measurement of a stated or identified dimension according to the intended usage. Such instances will be readily apparent to the skilled person from the context of the individual usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Stent delivery systems are generally known in the art. The assembly of such delivery systems, however, often may be complicated. In particular, although it is common practice to load a stent into a delivery sheath during assembly of a stent delivery system, currently available stent delivery systems often require that a stent be loaded onto the stent delivery system by collapsing and feeding a first end of the stent into a delivery sheath followed by the middle portion and then the opposing end, thereby elongating the stent as it is collapsed and fed into the delivery sheath. However, assembling the stent onto the stent delivery system in this way may cause undesirable folding and/or deformation of the stent, particularly at the end(s). Such folding and/or deformation of the stent and/or the end(s) during loading of the stent may result in later folding and/or deformation in vivo, which may lead to obstruction of the vessel lumen. Accordingly, there is a need for improved methods of loading the stent into the stent delivery system during assembly of the same.

This disclosure pertains to devices or systems for deploying a stent, or other device as described herein, in a bodily passageway. Deployment may be achieved for medical applications (e.g., endoscopic therapy, etc.) in the gastrointestinal tract, the biliary tract, the urinary tract, and/or the respiratory tract. Moreover, the assembly devices may be deployed in the neurological system (e.g., in the brain) and/or in the cardiovascular system (e.g., in the heart, veins, and/or arteries). Reference to bodily passageways and/or lumens may be to passageways and/or lumens in any of the aforementioned tracts and systems or elsewhere in the body.

Generally speaking, any suitable stent may be used with the methods and/or devices of the present disclosure. In particular, various stent types and stent constructions may be employed in the invention. The various stents useful herewith may include, without imitation, self-expanding stents. The stents may be capable of radially contracting or collapsing as well and in this sense can best be described as radially distensible or deformable. Self-expanding stents may include those that have a spring-like action which causes the stent to radially expand when unconstrained, or stents which expand due to shape memory properties of the stent material for a particular configuration at a certain temperature. The configuration of the stent may also be chosen from a host of geometries. For example, wire stents may be fastened into a continuous helical pattern, with or without a wave or zig-zag-like pattern in the wire, to form a radially deformable and/or expandable stent. Individual rings or circular members may be linked together such as by struts, sutures, and/or welding, interlacing, or locking of the rings to form a tubular stent. Tubular stents useful in the disclosure may also include those formed by etching or cutting a pattern from a tube. Such stents are often referred to as slotted or cut stents. Furthermore, stents may be formed by etching a pattern into a material or mold and depositing stent material in the pattern, such as by chemical vapor deposition or the like.

In some embodiments, braided, woven, helical coil, and/or laser-cut stents may be useful. Braided, woven, and/or helical coil stents may be formed by arranging filaments over a mandrel, for example. The stent may be capable of being radially compressed and longitudinally extended (e.g., to a delivery configuration) for loading into a delivery device and/or implantation into a body lumen. In some embodiments, the stent may have a unitary structure. In some embodiments, filaments of the stent may be mechanically secured by welding, suturing, or other securement means.

The stent may have one or more atraumatic open end(s). As used herein, the phrase "atraumatic end", and its variants, refers to a terminal end of the stent which is free of sharp wire ends or other sharp projections or deformities which may cause trauma when implanted into a bodily lumen. In some embodiments, the filaments of the stent may be braided so as to produce an atraumatic end. For example, certain filaments of the stent may be extended and looped back to provide an atraumatic end devoid of, for example, sharp or traumatically pointed bends, sharp wire ends, and other traumatically sharp projections or deformities or the like. In some embodiments, the end(s) of the stent may optionally flare radially outward from a body or middle portion of the stent in an expanded configuration of the stent, and/or the end(s) of the stent may optionally have a greater outer diameter or extent than the body or middle portion of the stent in the expanded configuration.

In some embodiments, the stent may include a covering disposed over a longitudinal length or a portion of the longitudinal length of the stent. In some embodiments, the stent may include a liner disposed within the longitudinal length or a portion of the longitudinal length of the stent. In some embodiments, the stent may include both a covering and a liner disposed over and within the longitudinal length or a portion of the longitudinal length of the stent. In some embodiments, the covering and/or the liner may be a unitary film or coating that embeds or partially embeds the stent. In some embodiments, the covering and/or the liner may be in the form of a tubular structure. Some suitable but non-limiting materials for the covering and/or the liner, for example polymeric materials or textile materials, are described below.

In FIG. 1, an example delivery device 100 including an elongate outer sheath 110, an inner shaft 120 slidably disposed within a lumen of the elongate outer sheath 110, and a distal atraumatic tip 130 fixedly attached to a distal end of the inner shaft 120 is illustrated receiving an example expandable stent 200. The distal atraumatic tip 130 may be configured to engage a distal end of the elongate outer sheath 110. The elongate outer sheath 110 may be configured to receive the expandable stent 200 in a radially compressed and/or elongated configuration (e.g., in a delivery configuration) within a distal end and/or distal portion of the elongate outer sheath 110. In some embodiments, the inner shaft 120 and the distal atraumatic tip 130 may optionally include a lumen extending therethrough, the lumen being configured to accept and/or slide over a guidewire. In at least some embodiments, the inner shaft 120 may include a stop and/or pusher element 140 disposed proximate a distal portion of the inner shaft 120, the distal portion being configured to receive the expandable stent 200 disposed on and/or over the distal portion distal of the stop and/or pusher element 140 and/or proximal of the distal atraumatic tip 130. In other words, the expandable stent 200 may be disposed between the stop and/or pusher element 140 and the distal atraumatic tip 130 on and/or over the distal portion of the inner shaft 120. Some suitable but non-limiting materials for the delivery device 100, the elongate outer sheath 110, the inner shaft 120, the distal atraumatic tip 130, and/or the stop and/or pusher element 140, for example metallic and/or polymeric materials, are described below.

The expandable stent 200 may include a middle portion 210 disposed between a first end 220 and a second end 230. In at least some embodiments, the first end 220 of the expandable stent 200 may be a proximal end of the expandable stent 200 and the second end 230 of the expandable stent 200 may be a distal end of the expandable stent 200.

In some embodiments, the expandable stent 200 may have and/or be configured to shift between an expanded configuration and a constrained configuration. In some embodiments, the expandable stent 200 may be configured to self-expand toward the expanded configuration when unconstrained. In some embodiments, the expandable stent 200 may be configured to be mechanically and/or forcibly expanded toward the expanded configuration, such as with a balloon or other expandable structure for example. In some embodiments, the expandable stent 200 may include a flared first end 220 and/or a flared second end 230, wherein in the expanded configuration of the expandable stent 200, the first end 220 of the expandable stent 200 and/or the second end 230 of the expandable stent 200 has a greater outer extent and/or outer diameter than the middle portion 210 of the expandable stent 200. Constructional details of the expandable stent 200 may include one or more of the features, arrangements, and/or configurations described above. Some suitable but non-limiting materials for the expandable stent 200, for example metallic and/or polymeric materials, are described below.

Figure 2:
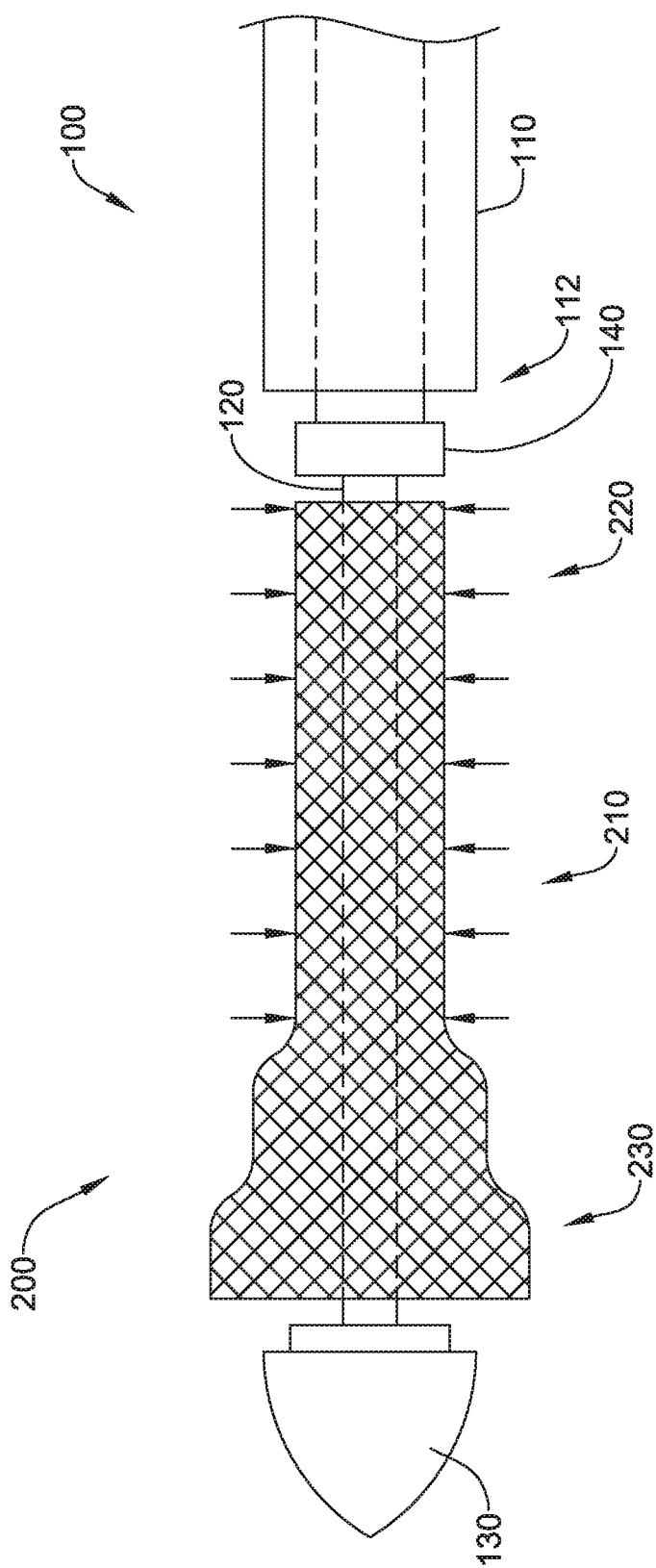

In some embodiments, a method of loading the expandable stent 200 into the delivery device 100 may include radially compressing and/or collapsing the middle portion 210 of the expandable stent 200 before any other portion of the expandable stent 200, as seen in FIG. 1. In at least some embodiments, the inner shaft 120 of the delivery device 100 may be disposed through a lumen of the expandable stent 200 before the middle portion 210 of the expandable stent 200 is radially compressed and/or collapsed to the constrained configuration. In some embodiments, a maximum outer extent and/or outer diameter of the expandable stent 200 in the constrained configuration may be less than an inner diameter of the elongate outer sheath 110 at the distal end 112 of the elongate outer sheath 110. In some embodiments, the method of loading the expandable stent 200 into the delivery device 100 may include radially compressing the expandable stent 200 from the middle portion 210 of the expandable stent 200 toward the first end 220 of the expandable stent 200, as seen in FIG. 2 for example. In an expandable stent 200 having a flared first end 220 and/or a flared second end 230, radially compressing and/or collapsing the middle portion 210 of the expandable stent 200 first may be easier to accomplish (e.g., require less force, etc.) than radially compressing and/or collapsing one of the larger flared ends first, thereby encouraging uniform collapse of the expandable stent 200 as the expandable stent 200 is shifted into the constrained configuration.

Figure 3:
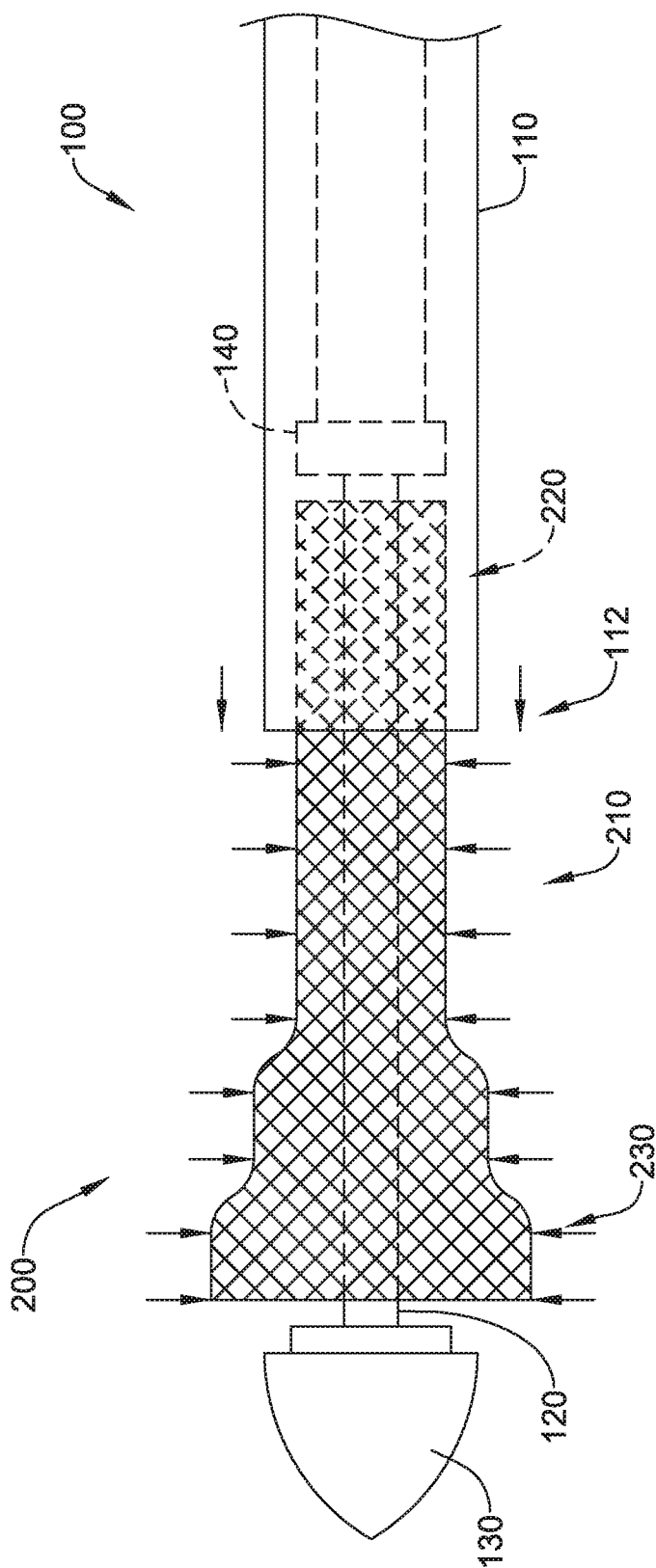
Figure 4:
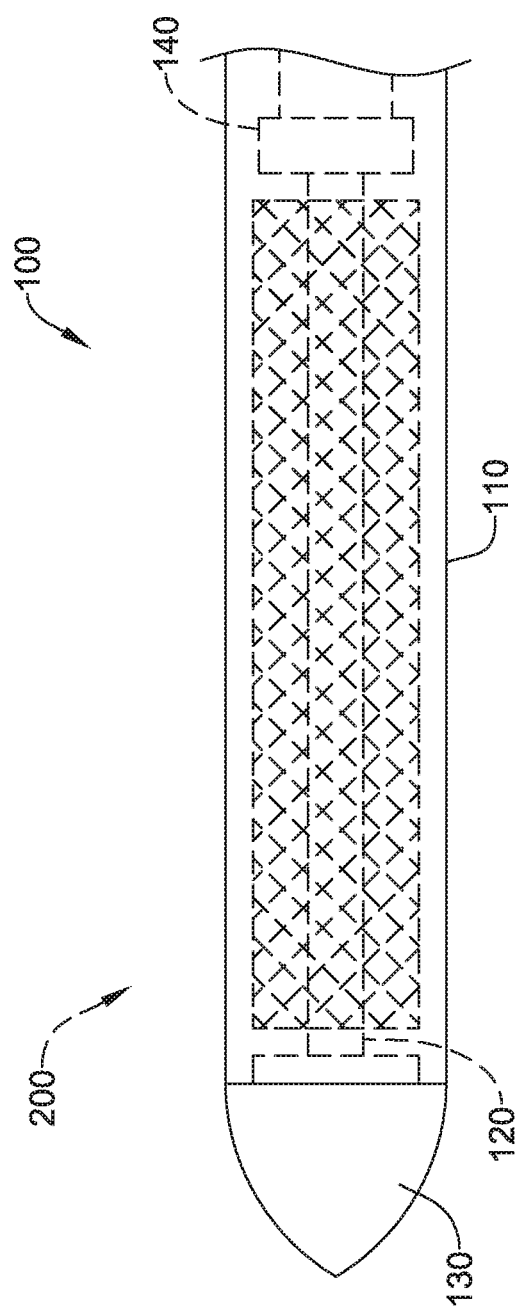

Thereafter, the method of loading the expandable stent 200 into the delivery device 100 may include inserting the first end 220 of the expandable stent 200 followed by the middle portion 210 of the expandable stent 200 into the distal end 112 of the elongate outer sheath 110 of the delivery device 100 in the constrained configuration, as shown in FIG. 3 for example. FIG. 4 illustrates the expandable stent 200 in the constrained configuration disposed within the distal end 112 of the elongate outer sheath 110 of the delivery device 100, with the distal atraumatic tip 130 engaged with the distal end 112 of the elongate outer sheath 110 of the delivery device 100. In this arrangement, the delivery device 100 may be navigated, for example percutaneously, to a treatment site within a patient. The stop and/or pusher element 140 may be configured to engage the first end 220 of the expandable stent 200 and push the expandable stent 200 distally out of the elongate outer sheath 110, for example at the treatment site, upon relative movement between the elongate outer sheath 110 and the inner shaft 120.

Radially compressing the middle portion 210 of the expandable stent 200 and/or the expandable stent 200 from the middle portion 210 of the expandable stent 200 toward the first end 220 of the expandable stent 200 for example, may be accomplished in several different ways, some of which will be described below. In one example, all steps and/or aspects of radially compressing the expandable stent 200 may be done manually, for example, by and/or using a person's hands. Some other non-limiting examples, such as using a collapsing fixture, are described below.

Figure 5:
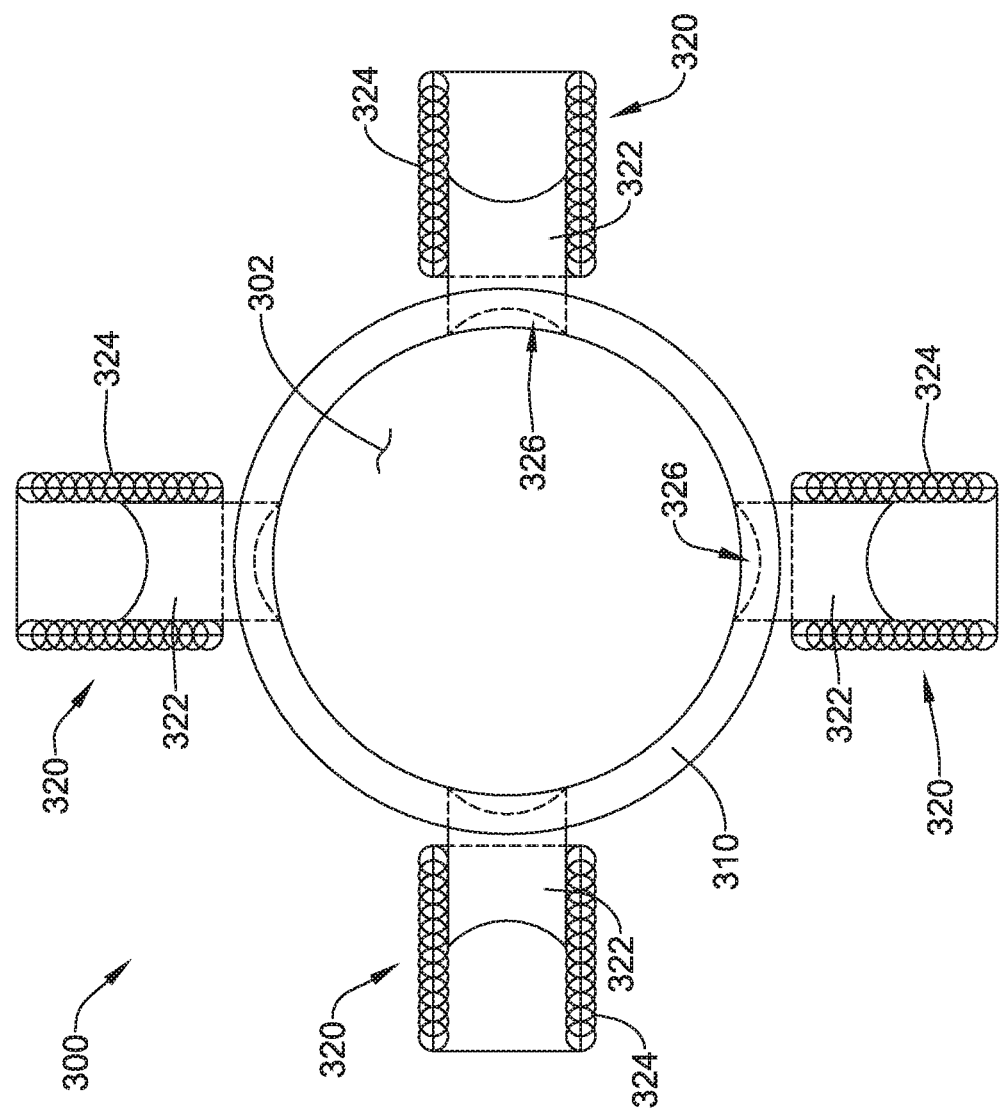
FIG. 5 illustrates an example collapsing fixture in an open configuration.
Figure 6:
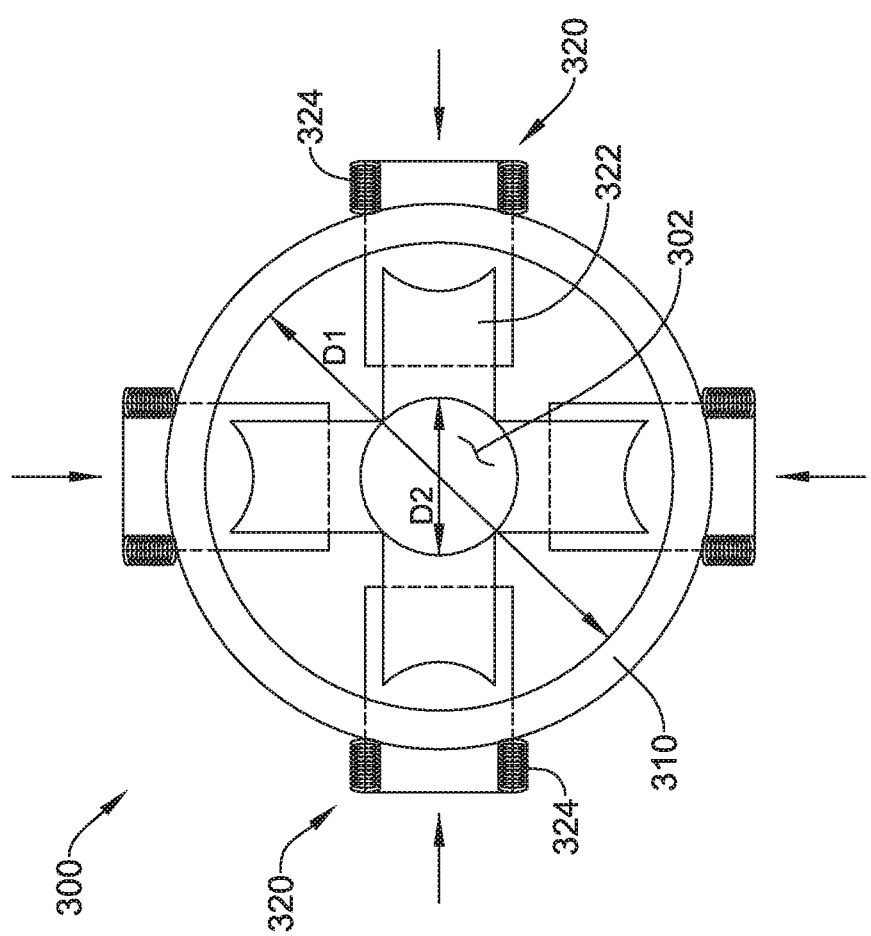
FIG. 6 illustrates the example collapsing fixture of FIG. 5 in a closed configuration.

FIGS. 5 and 6 illustrate an example collapsing fixture 300 in an open configuration and a closed configuration, respectively. In some embodiments, the collapsing fixture 300 may include an outer ring 310 and a plurality of movable elements 320 operatively connected to the outer ring 310. In some embodiments, the outer ring 310 may be an annular structure at least partially defining a passage 302 extending through the collapsing fixture 300 in the open configuration. In some embodiments, the outer ring 310 may have an inner diameter D1 sufficient and/or configured to accept and/or receive the expandable stent 200 in the expanded configuration within the passage 302.

In some embodiments, the plurality of movable elements 320 may be movably attached to the outer ring 310. The plurality of movable elements 320 may be configured to be actuated (e.g., moved and/or translated, etc.) radially inward relative to the outer ring 310 and/or a central axis of the passage 302 to radially compress the expandable stent 200 disposed within the passage 302 in the closed configuration. In other words, the collapsing fixture 300 may be configured to radially collapse the expandable stent 200 (e.g., any portion of the expandable stent 200 disposed within the collapsing fixture 300 and/or within or surrounded by the plurality of movable elements 320) from the expanded configuration toward the constrained configuration as the collapsing fixture 300 is shifted from the open configuration to the closed configuration. In some embodiments, each of the plurality of movable elements 320 may be arranged, arrayed, spaced, and/or positioned equidistantly around the outer ring 310 and/or the central axis of the passage 302. In some embodiments, the plurality of movable elements 320 may be arranged, spaced, and/or positioned at irregular intervals around the outer ring 310 and/or the central axis of the passage 302.

In some embodiments, each of the plurality of movable elements 320 may include at least one spring 324 (e.g., compression spring, etc.) connected to the outer ring 310 (e.g., to an outer surface of the outer ring 310, etc.). The at least one spring 324 may be held in compression at a reduced overall length when the collapsing fixture 300 is in the closed configuration and the at least one spring 324 may be in a relaxed state (and/or under less compressive force than in the closed configuration) when the collapsing fixture is in the open configuration. Any suitable means of actuation may be utilized (e.g., manually-actuated, spring-actuated, hydraulically-actuated, pneumatically-actuated, electrically-actuated, etc.) to shift the collapsing fixture 300 from the open configuration to the collapsed configuration. Alternatively, configurations devoid of the at least one spring 324 and relying upon one or more other means of actuation are also contemplated.

In some embodiments, each of the plurality of movable elements 320 includes a concave profile 326 configured to contact the expandable stent 200 in the closed configuration and/or as the collapsing fixture 300 is shifted from the open configuration to the closed configuration. In some embodiments, the concave profile 326 may generally correspond to a radius of curvature of an outer surface of the expandable stent 200 in the constrained configuration. Therefore, when the collapsing fixture 300 is in the closed configuration, a combined radius of curvature of the concave profile(s) 326 of each of the plurality of movable elements 320 may generally define a reduced inner diameter D2 corresponding to and/or generally equal to a radius of curvature and/or an outer diameter of the expandable stent 200 in the constrained configuration.

In some embodiments, each of the plurality of movable elements 320 includes a rolling element 322 proximate the outer ring 310 in the open configuration. In some embodiments, when the expandable stent 200 is disposed within the collapsing fixture 300 and/or the passage 302 in the open configuration, each rolling element 322 is spaced apart from the expandable stent 200. In some embodiments, each rolling element 322 includes the concave profile 326 configured to contact the expandable stent 200 in the closed configuration and/or as the collapsing fixture 300 is shifted from the open configuration to the closed configuration. In some embodiments, each rolling element 322 may include a wheel or other rotating structure having an axis of rotation perpendicular to and laterally offset from the central axis of the passage 302.

Figure 7:
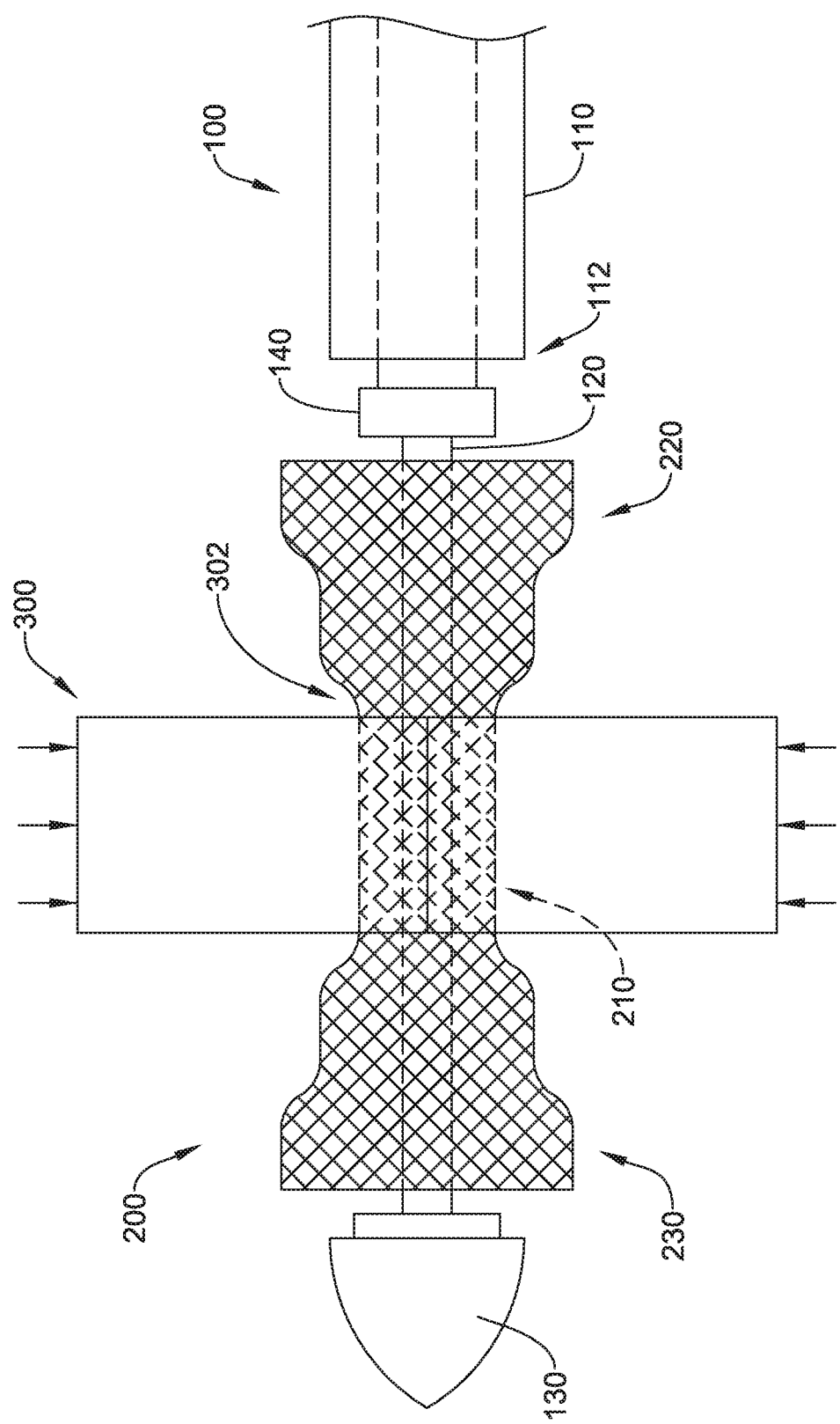
FIGS. 7-9 illustrate the example method of loading the stent into the delivery device using the collapsing fixture of FIGS. 5 and 6.

A method of loading the expandable stent 200 into the delivery device 100 using the collapsing fixture 300 may include radially compressing the middle portion 210 of the expandable stent 200 before the first end 220 of the expandable stent 200 and/or before any other portion of the expandable stent 200, which step may include positioning the middle portion 210 of the expandable stent 200 within the passage 302 extending through the collapsing fixture 300 with the first end 220 of the expandable stent positioned outside of the passage 302. Positioning the middle portion 210 of the expandable stent 200 within the passage 302 of the collapsing fixture 300 may occur when the collapsing fixture 300 is in the open configuration. Thereafter, the collapsing fixture 300 may be shifted from the open configuration to a closed configuration with the expandable stent 200 positioned therein, thereby collapsing the middle portion 210 of the expandable stent 200 before the first end 220 of the expandable stent 200 and/or before any other portion of the expandable stent 200, as seen in FIG. 7. In at least some embodiments, the inner shaft 120 of the delivery device 100 may be disposed through a lumen of the expandable stent 200 before the middle portion 210 of the expandable stent 200 is positioned within the passage 302 and/or before the middle portion 210 of the expandable stent 200 is radially compressed and/or collapsed toward the constrained configuration.

Figure 8:
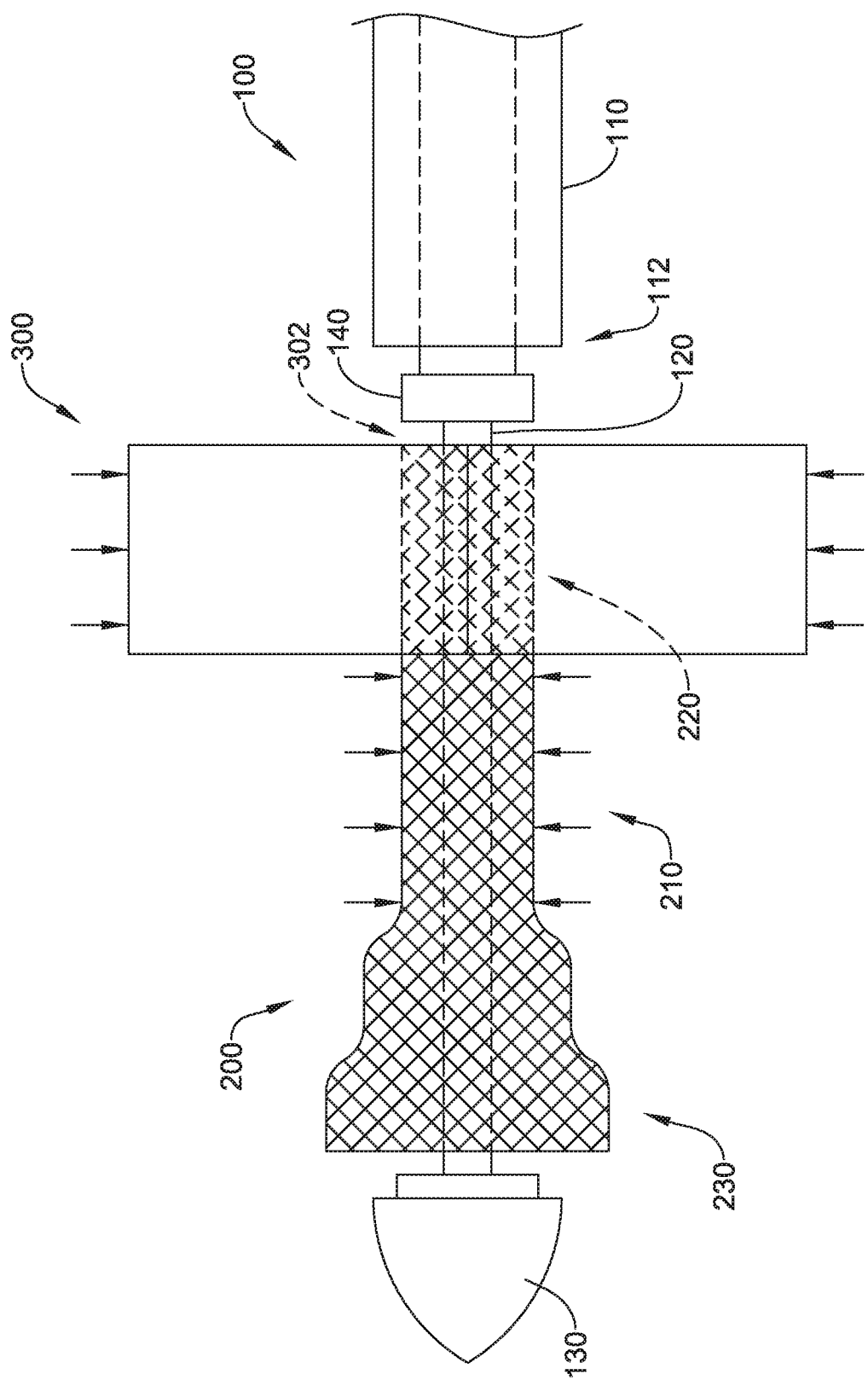

After shifting the collapsing fixture 300 to the closed configuration and/or after radially compressing and/or collapsing the middle portion 210 of the expandable stent 200, the method may include moving the collapsing fixture 300 relative to the expandable stent 200 such that the passage 302 extending through the collapsing fixture 300 and/or the collapsing fixture 300 is moved from the middle portion 201 of the expandable stent 200 toward the first end 220 of the expandable stent 200, thereby radially compressing and/or collapsing the expandable stent 200 from the middle portion 210 toward the first end 220 of the expandable stent 200 such that the first end 220 of the expandable stent 200 is radially compressed and/or collapsed within the passage 302 to the constrained configuration, as shown in FIG. 8 for example.

Figure 9:
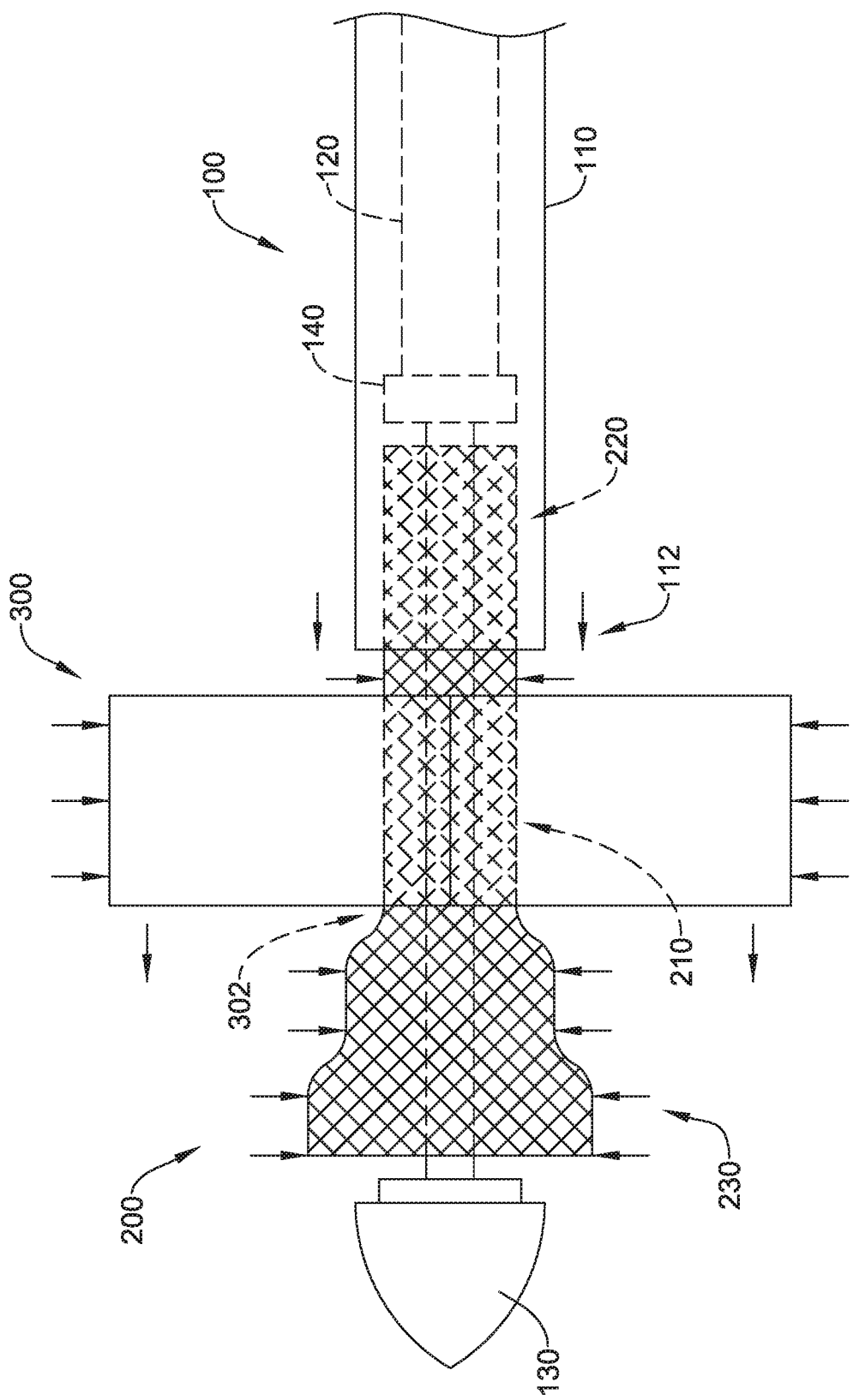

The method may thereafter include advancing the first end 220 of the expandable stent 200 followed by the middle portion 210 of the expandable stent 200 into the distal end 112 of the elongate outer sheath 110 of the delivery device 100 while at least a portion of the expandable stent 200 is disposed within the passage 302 of the collapsing fixture 300, as seen in FIG. 9 for example. In some embodiments, the method may further include maintaining the expandable stent 200 in a fixed position and moving the collapsing fixture 300 axially away from the first end 220 of the expandable stent 200 and toward the second end 230 of the expandable stent 200 as the first end 220 of the expandable stent 200 is advanced into the distal end 112 of the elongate outer sheath 110. As the collapsing fixture 300 is moved away from the first end 220 of the expandable stent 200 and toward the second end 230 of the expandable stent 200, the middle portion 210 of the expandable stent 200 passes back through the collapsing fixture 300, and then the expandable stent 200 is radially compressed and/or collapsed from the middle portion 210 of the expandable stent 200 toward the second end 230 of the expandable stent 200 such that the second end 230 of the expandable stent 200 is radially compressed and/or collapsed to the constrained configuration. The elongate outer sheath 110 may be advanced over the expandable stent 200 and/or the expandable stent 200 may be inserted into the distal end 112 of the elongate outer sheath 110 until the entire expandable stent 200 is disposed within the elongate outer sheath 110 in the constrained configuration, as shown earlier in FIG. 4 for example.

Figure 10:
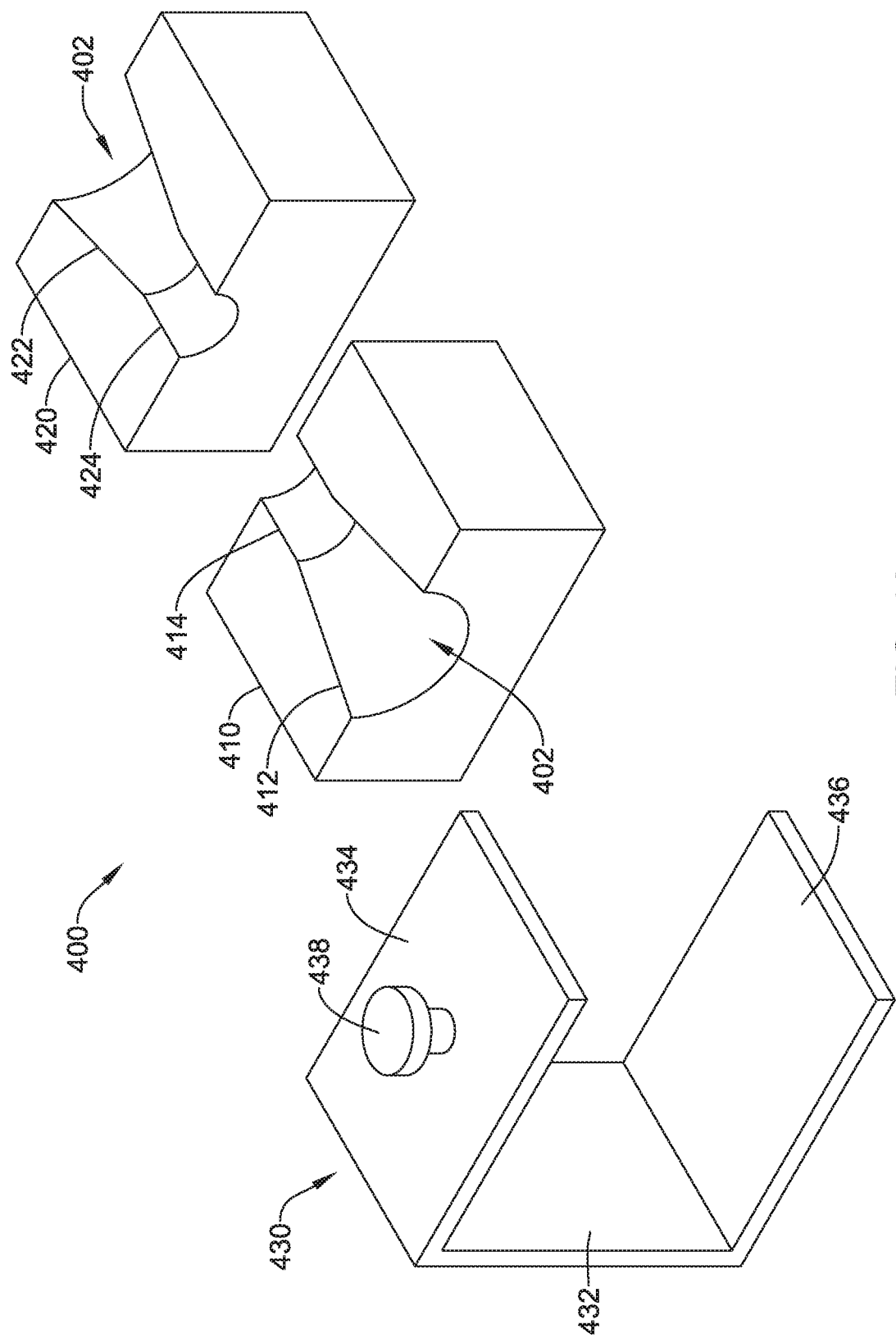
FIG. 10 illustrates an example collapsing fixture in an open configuration.
Figure 11:
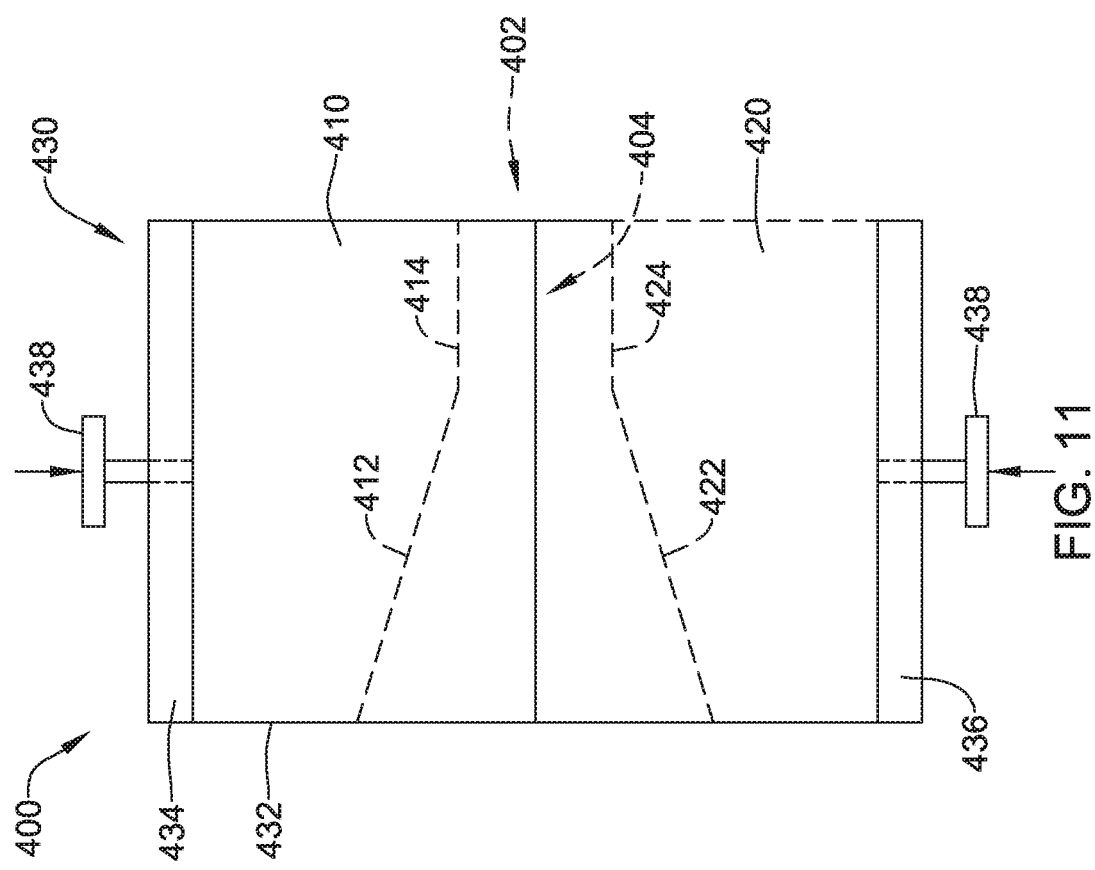
FIG. 11 illustrates the example collapsing fixture of FIG. 10 in a closed configuration.

FIGS. 10 and 11 illustrate an example collapsing fixture 400 in an open configuration and a closed configuration, respectively. The collapsing fixture 400 may include a first block portion 410, a second block portion 420, and a clamping portion 430. The first block portion 410 may be configured to engage the second block portion 420 in the closed configuration, the first block portion 410 and the second block portion 420 cooperating to at least partially define a passage 402 through the collapsing fixture 400. In some embodiments, the clamping portion 430 may comprise a substantially U-shaped structure having a base portion 432, a first leg portion 434 extending away from the base portion 432 in a first direction generally perpendicular to the base portion 432, and a second leg portion 436 extending away from the base portion 432 in the first direction generally perpendicular to the base portion 432. The first leg portion 434 and the second leg portion 436 may be spaced apart from each other and cooperate with the base portion 432 to define a receptacle for receiving the first block portion 410 and the second block portion 420.

The clamping portion 430 may be configured to retain the first block portion 410 in engagement with the second block portion 420 within the receptacle when the collapsing fixture 400 is in the closed configuration. For example, the clamping portion 430 may include at least one securement member 438 configured to secure the first block portion 410 and the second block portion 420 in engagement with each other as well as in engagement with the clamping portion 430. In some embodiments, each of the first leg portion 434 and the second leg portion 436 may include at least one securement member 438. In some embodiments, the at least one securement member 438 may be a threaded member, a cam member, a latching member, a pin member, a spring-loaded member, or other suitable securement member configured to secure and retain the first block portion 410 in engagement with the second block portion 420.

The first block portion 410 may include a first tapered portion 412 and a first channel portion 414 cooperating to at least partially define the passage 402. The second block portion 420 may include a second tapered portion 422 and a second channel portion 424 cooperating to at least partially define the passage 402. When the first block portion 410 is engaged with the second block portion 420, the first tapered portion 412 may align with and/or cooperate with the second tapered portion 422, and the first channel portion 414 may align with and/or cooperate with the second channel portion 424. In at least some embodiments, the first tapered portion 412 and the second tapered portion 422 may cooperate to form a generally conical shape having an increased diameter at an edge or outer surface of the first block portion 410 and the second block portion 420, and a reduced diameter within an interior of the first block portion 410 and the second block portion 420 at a junction and/or intersection with the first channel portion 414 and the second channel portion 424. Other shapes and/or configurations (e.g., arcuate surfaces, curved surfaces, etc.) are also contemplated. In some embodiments, the first channel portion 414 of the first block portion 410 may cooperate with the second channel portion 424 of the second block portion 420 to form a reduced diameter portion 404 of the passage 402, wherein the reduced diameter portion 404 is configured to radially compress and/or collapse a portion of the expandable stent 200 disposed therein.

Figure 12:
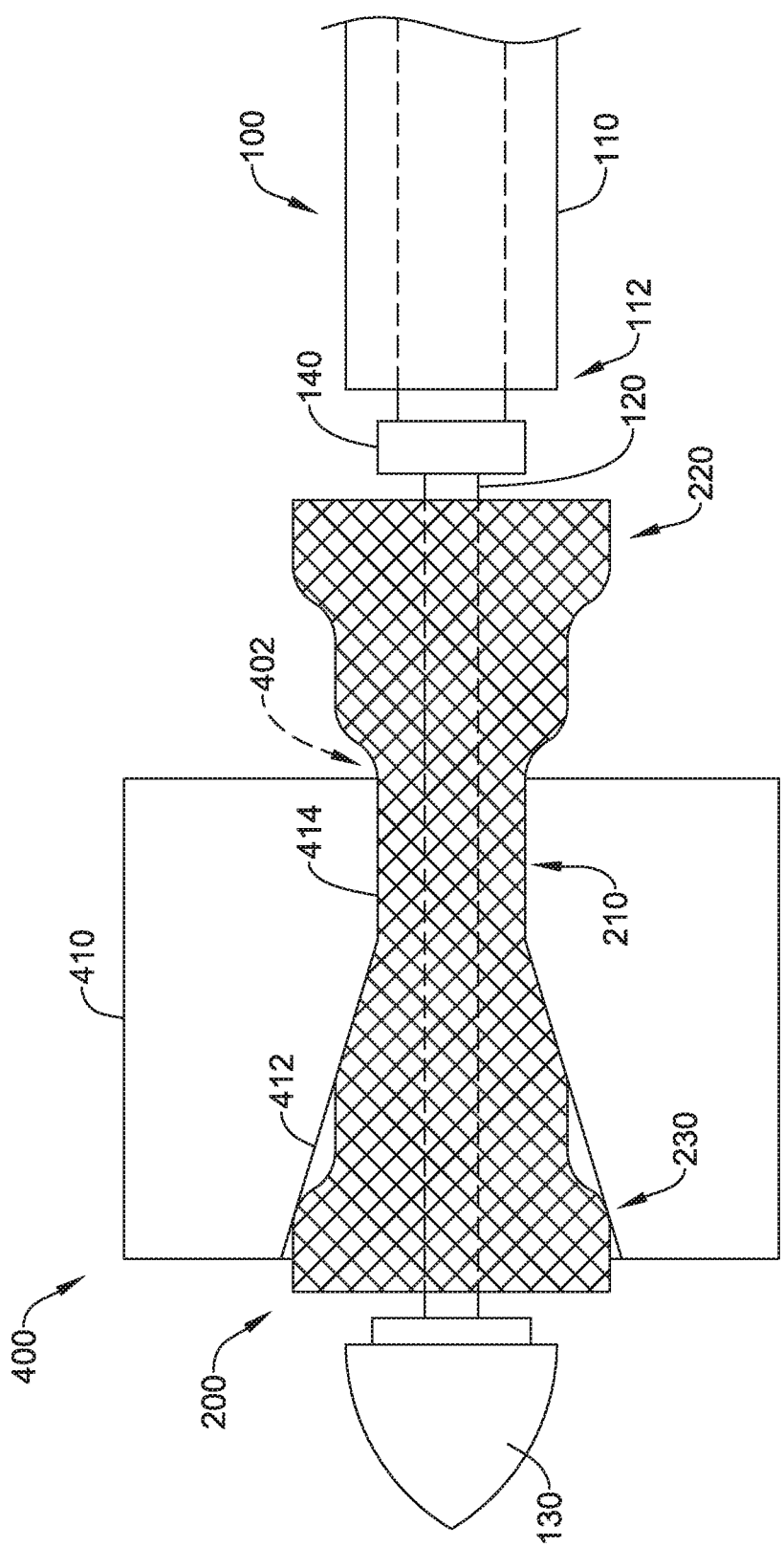
FIGS. 12-14 illustrate the example method of loading the stent into the delivery device using the collapsing fixture of FIGS. 10 and 11.

A method of loading the expandable stent 200 into the delivery device 100 using the collapsing fixture 400 may include radially compressing the middle portion 210 of the expandable stent 200 before the first end 220 of the expandable stent 200 and/or before any other portion of the expandable stent 200, which step may include positioning the middle portion 210 of the expandable stent 200 within the passage 402 extending through the collapsing fixture 400 with the first end 220 of the expandable stent positioned outside of the passage 402. Positioning the middle portion 210 of the expandable stent 200 within the passage 402 of the collapsing fixture 400 may occur when the collapsing fixture 400 is in the open configuration. For example, positioning the middle portion 210 of the expandable stent 200 within the passage 402 of the collapsing fixture 400 may include positioning the middle portion 210 of the expandable stent 200 in the first channel portion 414 of the first block portion 410, as seen in FIG. 12.

Thereafter, the collapsing fixture 400 may be shifted from the open configuration to a closed configuration with the expandable stent 200 positioned therein, thereby collapsing the middle portion 210 of the expandable stent 200 before the first end 220 of the expandable stent 200 and/or before any other portion of the expandable stent 200, by engaging the second block portion 420 with the first block portion 410, such that the middle portion 210 of the expandable stent 200 is positioned within the reduced diameter portion 404 of the passage 402. In at least some embodiments, the inner shaft 120 of the delivery device 100 may be disposed through a lumen of the expandable stent 200 before the middle portion 210 of the expandable stent 200 is positioned within the passage 402 and/or before the middle portion 210 of the expandable stent 200 is radially compressed and/or collapsed toward the constrained configuration. In at least some embodiments, shifting the collapsing fixture 400 from the open configuration to the closed configuration may include disposing and/or positioning the first block portion 410 and the second block portion 420 engaged thereto within the receptacle of the clamping portion 430. In some embodiments, the at least one securement member 438 may be actuated and/or used to secure the first block portion 410 and the second block portion 420 in engagement with each other as well as in non-movable engagement with the clamping portion 430.

Figure 13:
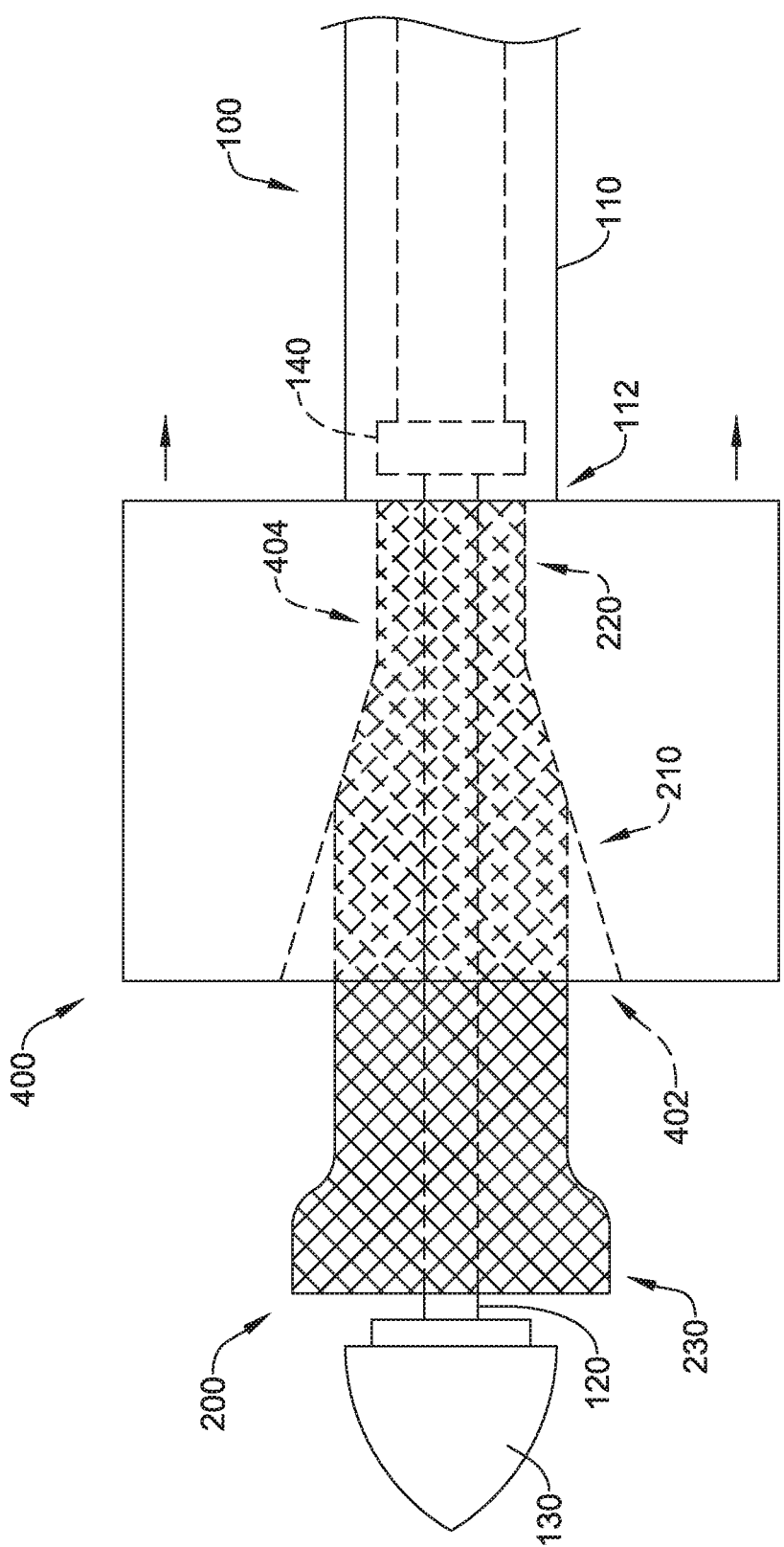

After shifting the collapsing fixture 400 to the closed configuration and/or after radially compressing and/or collapsing the middle portion 210 of the expandable stent 200, the method may include moving the collapsing fixture 400 relative to the expandable stent 200 such that the passage 402 extending through the collapsing fixture 400 and/or the collapsing fixture 400 is moved from the middle portion 210 of the expandable stent 200 toward the first end 220 of the expandable stent 200, thereby radially compressing and/or collapsing the expandable stent 200 from the middle portion 210 toward the first end 220 of the expandable stent 200 such that the first end 220 of the expandable stent 200 is radially compressed and/or collapsed within the passage 402 to the constrained configuration, as shown in FIG. 13 for example.

Figure 14:
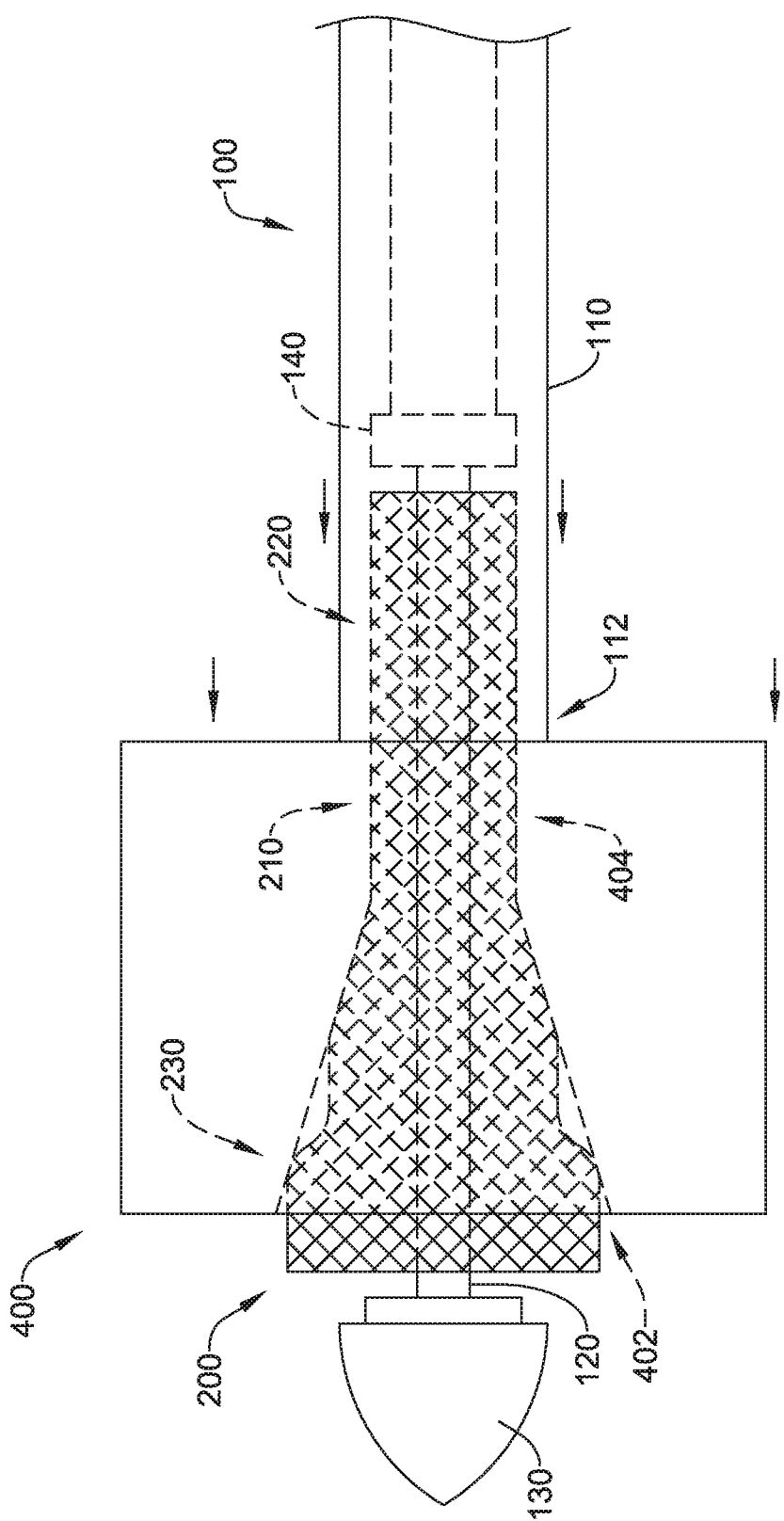

The method may thereafter include advancing the first end 220 of the expandable stent 200 followed by the middle portion 210 of the expandable stent 200 into the distal end 112 of the elongate outer sheath 110 of the delivery device 100 while at least a portion of the expandable stent 200 is disposed within the passage 402 of the collapsing fixture 400, as seen in FIG. 14 for example. In some embodiments, the method may include maintaining the expandable stent 200 in a fixed position and moving the collapsing fixture 400 axially away from the first end 220 of the expandable stent 200 and toward the second end 230 of the expandable stent 200 as the first end 220 of the expandable stent 200 is advanced and/or inserted into the distal end 112 of the elongate outer sheath 110. As the collapsing fixture 400 is moved away from the first end 220 of the expandable stent 200 and toward the second end 230 of the expandable stent 200, the middle portion 210 of the expandable stent 200 passes back through the collapsing fixture 400, and then the expandable stent 200 is radially compressed and/or collapsed from the middle portion 210 of the expandable stent 200 toward the second end 230 of the expandable stent 200 such that the second end 230 of the expandable stent 200 is radially compressed and/or collapsed to the constrained configuration. The elongate outer sheath 110 may be advanced over the expandable stent 200 and/or the expandable stent 200 may be inserted into the distal end 112 of the elongate outer sheath 110 until the entire expandable stent 200 is disposed within the elongate outer sheath 110 in the constrained configuration, as shown earlier in FIG. 4 for example.

Figure 15:
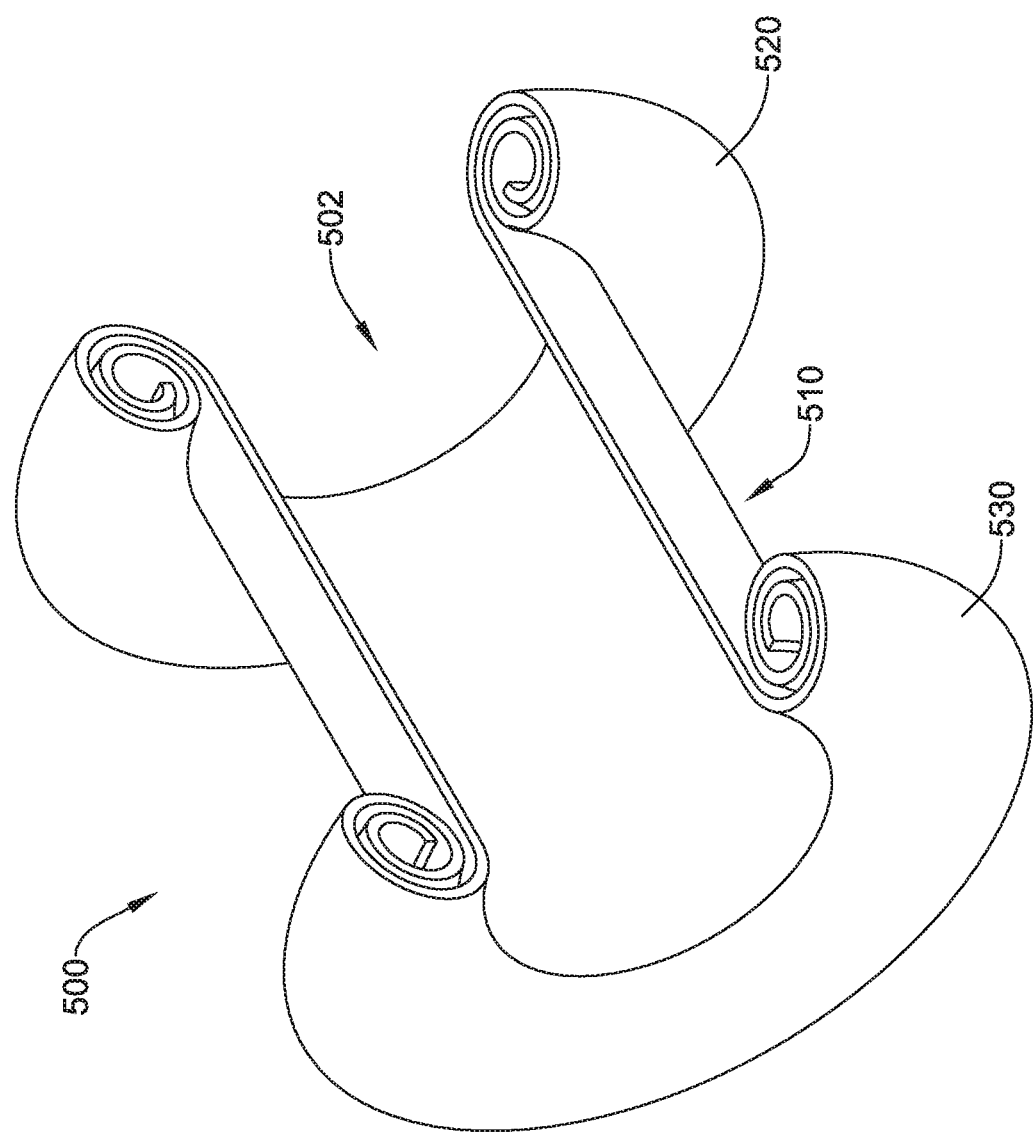
FIG. 15 illustrates an example collapsing fixture in an open configuration.

FIG. 15 illustrates an example collapsing fixture 500 in an open configuration. The collapsing fixture 500 may include an annular collar 510 at least partially defining a passage 502 through the collapsing fixture 500. The annular collar 510 may include a sleeve portion 520 attached thereto at a first end of the annular collar 510. In at least some embodiments, the sleeve portion 520 is and/or includes a rolled material capable of being unrolled in a direction away from the annular collar 510. In some embodiments, the sleeve portion 520 includes an enlarged end 522 opposite the annular collar 510. The enlarged end 522 may be configured to accept the distal end 112 of the elongate outer sheath 110 therein to facilitate insertion of the first end 220 of the expandable stent 200 into the distal end 112 of the elongate outer sheath 110. In some embodiments, the annular collar 510 further includes a second sleeve portion 530 attached thereto at a second end of the annular collar 510 opposite the first end of the annular collar 510 and/or the sleeve portion 520. As will be discussed further below, the sleeve portion 520 may be extendable in a first direction away from the annular collar 510 and/or parallel to a central axis of the passage 502, and/or the second sleeve portion 530 may be extendable in a second direction away from the annular collar 510 and/or parallel to the central axis of the passage 502. In at least some embodiments, the second direction may be opposite the first direction.

A method of loading the expandable stent 200 into the delivery device 100 using the collapsing fixture 500 may include radially compressing the middle portion 210 of the expandable stent 200 before the first end 220 of the expandable stent 200 and/or before any other portion of the expandable stent 200, which step may include positioning the middle portion 210 of the expandable stent 200 within the passage 502 extending through the collapsing fixture 500 with the first end 220 of the expandable stent positioned outside of the passage 502. Positioning the middle portion 210 of the expandable stent 200 within the passage 502 of the collapsing fixture 500 may occur when the collapsing fixture 500 is in the open configuration. For example, positioning the middle portion 210 of the expandable stent 200 within the passage 502 of the collapsing fixture 500 may include positioning the middle portion 210 of the expandable stent 200 within the annular collar 510 when the collapsing fixture 500 (and/or the annular collar 510) is in the open configuration.

Figure 16:
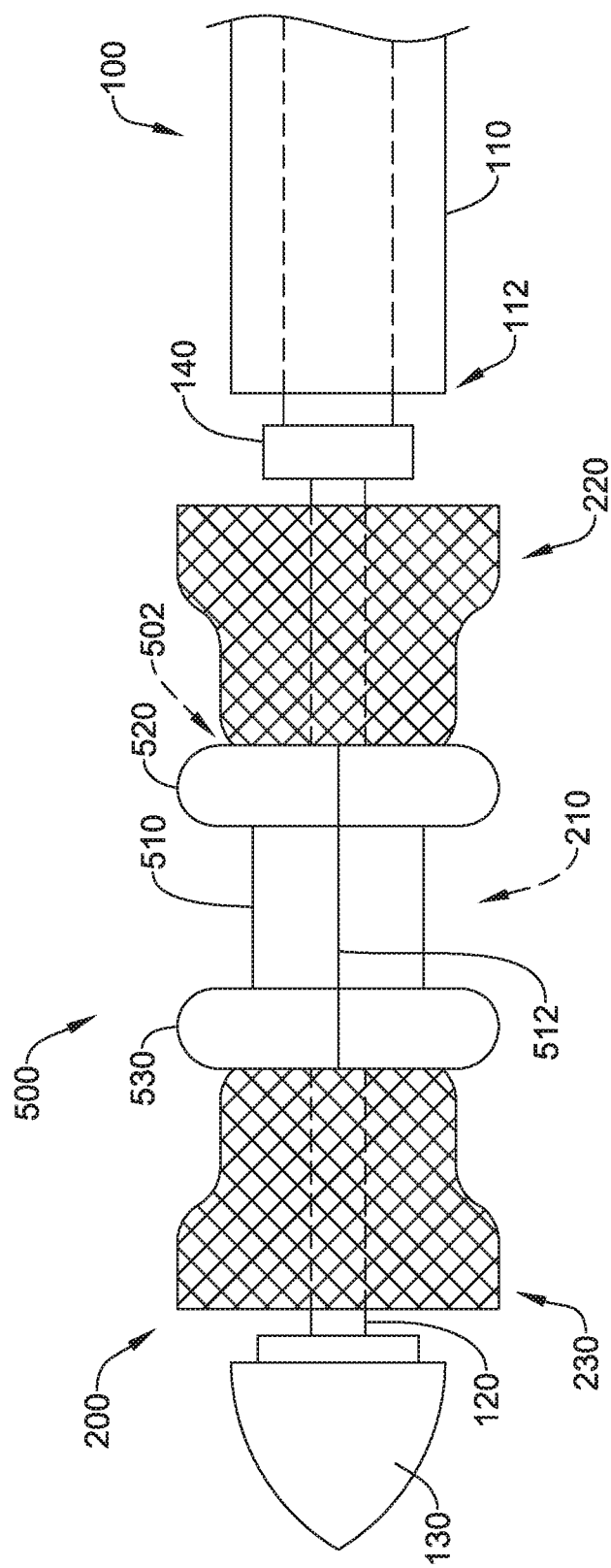
FIGS. 16-18 illustrate the example method of loading the stent into the delivery device using the collapsing fixture of FIG. 15.

Thereafter, the collapsing fixture 500 may be shifted from the open configuration to a closed configuration with the expandable stent 200 positioned therein, thereby radially compressing and/or collapsing the middle portion 210 of the expandable stent 200 before the first end 220 of the expandable stent 200 and/or before any other portion of the expandable stent 200, by closing the annular collar 510 with the middle portion 210 of the expandable stent 200 positioned within the passage 502 and/or the annular collar 510, as seen in FIG. 16 for example. In at least some embodiments, the inner shaft 120 of the delivery device 100 may be disposed through a lumen of the expandable stent 200 before the middle portion 210 of the expandable stent 200 is positioned within the passage 502 and/or the annular collar 510, and/or before the middle portion 210 of the expandable stent 200 is radially compressed and/or collapsed toward the constrained configuration. In at least some embodiments, shifting the collapsing fixture 500 from the open configuration to the closed configuration may include joining opposing sides of a seam or joint 512 extending generally parallel to a central axis of the passage 502.

Closure and/or joining opposing sides of the seam or joint 512 may be accomplished in a number of ways. In some embodiments, the opposing sides of the seam or joint 512 may be fused together along the seam or joint 512. In some embodiments, a mechanical closure means may be employed to join the opposing sides of the seam or joint 512. In some embodiments, the annular collar 510 may include and/or be formed from a material having shape memory properties, and/or a material that is crimpable or otherwise capable of retaining a particular shape or form such that as the annular collar 510 and/or the collapsing fixture 500 is shifted from the open configuration to the closed configuration, the annular collar 510 and/or the collapsing fixture 500 maintains and/or is self-biased to remain in the closed configuration. In some embodiments, the sleeve portion 520 and/or the second sleeve portion 530 may include an adhesive or bonding agent disposed thereon and/or embedded therein such that the opposing sides of the seam or joint 512 may be bonded together as the sleeve portion 520 and/or the second sleeve portion 530 is extended away from the annular collar 510. Other means of closing and/or joining the opposing sides of the seam or joint 512 are also contemplated and the examples listed herein are not intended to be limiting.

Figure 17:
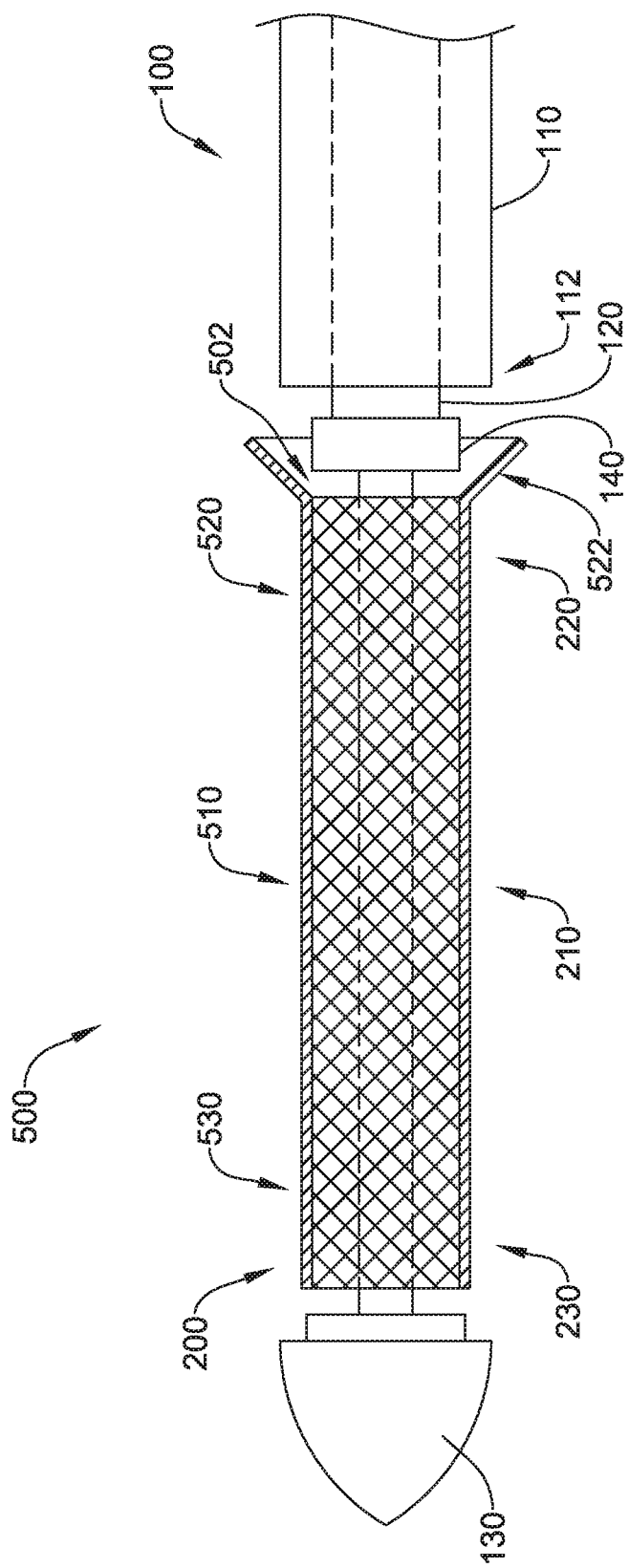

After shifting the collapsing fixture 500 to the closed configuration and/or after radially compressing and/or collapsing the middle portion 210 of the expandable stent 200 within the annular collar 510, the method may include extending the sleeve portion 520 toward the first end 220 of the expandable stent 200, thereby radially compressing and/or collapsing the expandable stent 200 from the middle portion 210 toward the first end 220 of the expandable stent 200 such that the first end 220 of the expandable stent 200 is radially compressed and/or collapsed within the passage 502 to the constrained configuration, as shown in FIG. 17 for example. For ease of understanding, the collapsing fixture 500 is shown in FIG. 17 in cross-section. Similarly, the method may include extending the second sleeve portion 530 toward the second end 230 of the expandable stent 200, thereby radially compressing and/or collapsing the expandable stent 200 from the middle portion 210 toward the second end 230 of the expandable stent 200 such that the second end 230 of the expandable stent 200 is radially compressed and/or collapsed within the passage 502 to the constrained configuration, as also shown in FIG. 17 for example. In at least some embodiments, the sleeve portion 520 may be a rolled material, and radially compressing and/or collapsing the expandable stent 200 from the middle portion 210 toward the first end 220 of the expandable stent 200 includes unrolling the sleeve portion 520 in the first direction toward the first end 220 of the expandable stent 200. In some embodiments, the second sleeve portion 530 may be a rolled material, and radially compressing and/or collapsing the expandable stent 200 from the middle portion 210 toward the second end 230 of the expandable stent 200 includes unrolling the second sleeve portion 530 in the second direction toward the second end 230 of the expandable stent 200. As the sleeve portion 520 and/or the second sleeve portion 530 is extended away from the annular collar 510 toward its respective end of the expandable stent 200, the seam or joint 512 extending generally parallel to a central axis of the passage 502 may extend commensurately and the sleeve portion 520 and/or the second sleeve portion 530 may be joined at and/or along the seam or joint 512 extending generally parallel to a central axis of the passage 502.

Figure 18:
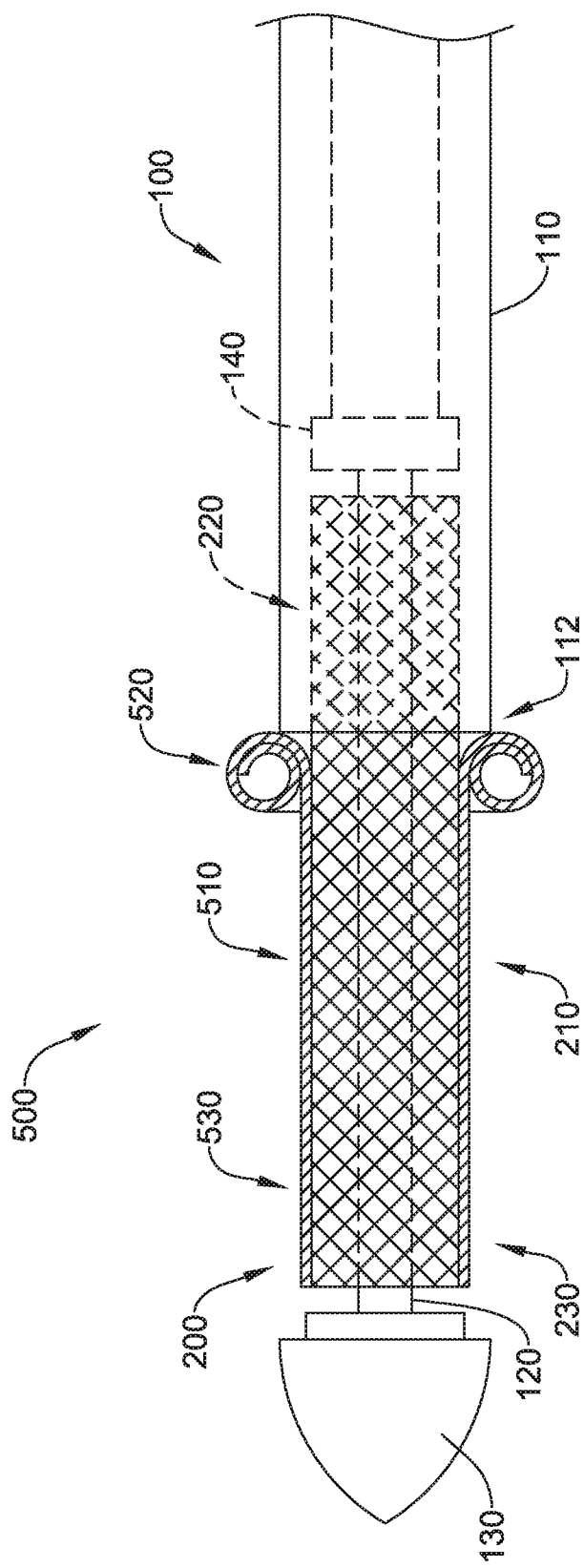

The method may thereafter include advancing the first end 220 of the expandable stent 200 followed by the middle portion 210 of the expandable stent 200 into the distal end 112 of the elongate outer sheath 110 of the delivery device 100 while at least a portion of the expandable stent 200 is disposed within the passage 502 of the collapsing fixture 500, as seen in FIG. 18 for example. For ease of understanding, the collapsing fixture 500 is shown in FIG. 18 in cross-section. In some embodiments, the method may include maintaining the expandable stent 200 in a fixed position and moving the collapsing fixture 500 axially away from the first end 220 of the expandable stent 200 and toward the second end 230 of the expandable stent 200 as the first end 220 of the expandable stent 200 is advanced and/or inserted into the distal end 112 of the elongate outer sheath 110. In some embodiments, moving the collapsing fixture 500 axially away from the first end 220 of the expandable stent 200 may include retracting, rolling, and/or peeling the sleeve portion 520 of the collapsing fixture 500 axially away from the first end 220 of the expandable stent 200 and toward the second end 230 of the expandable stent 200 as the first end 220 of the expandable stent 200 is advanced and/or inserted into the distal end 112 of the elongate outer sheath 110. The elongate outer sheath 110 may be advanced over the expandable stent 200 and/or the expandable stent 200 may be inserted into the distal end 112 of the elongate outer sheath 110 until the entire expandable stent 200 is disposed within the elongate outer sheath 110 in the constrained configuration, as shown earlier in FIG. 4 for example.

The materials that can be used for the various components of the delivery device 100, the expandable stent 200, the collapsing fixtures 300-500, etc. (and/or other systems disclosed herein) and the various elements thereof disclosed herein may include those commonly associated with medical devices. For simplicity purposes, the following discussion makes reference to the delivery device 100, the expandable stent 200, the collapsing fixtures 300-500, etc. However, this is not intended to limit the devices and methods described herein, as the discussion may be applied to other elements, members, components, or devices disclosed herein, such as, but not limited to, the elongate outer sheath 110, the inner shaft 120, the distal atraumatic tip 130, the outer ring 310, the plurality of movable elements 320, the rolling elements 322, the first block portion 410, the second block portion 420, the clamping portion 430, the annular collar 510, the sleeve portion 520, the second sleeve portion 530, and/or elements or components thereof.

In some embodiments, the delivery device 100, the expandable stent 200, the collapsing fixtures 300-500, etc., and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-superelastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery device 100, the expandable stent 200, the collapsing fixtures 300-500, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the delivery device 100, the expandable stent 200, the collapsing fixtures 300-500, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100, the expandable stent 200, the collapsing fixtures 300-500, etc. to achieve the same result.

In some embodiments, a degree of Magnetic Resonance Imaging (MRI) compatibility is imparted into the delivery device 100, the expandable stent 200, the collapsing fixtures 300-500, etc. For example, the delivery device 100, the expandable stent 200, the collapsing fixtures 300-500, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The delivery device 100, the expandable stent 200, the collapsing fixtures 300-500, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the delivery device 100, the expandable stent 200, the collapsing fixtures 300-500, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the delivery device 100, the expandable stent 200, the collapsing fixtures 300-500, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the delivery device 100, the expandable stent 200, the collapsing fixtures 300-500, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A method of loading an expandable stent into a delivery device, comprising:
   radially compressing a middle portion of the expandable stent before any other portion of the expandable stent;
   radially compressing the expandable stent from the middle portion toward a first end portion of the expandable stent; and
   thereafter, inserting the first end portion of the expandable stent followed by the middle portion of the expandable stent into a distal end of an elongate outer sheath of the delivery device.

2. The method of claim 1, wherein radially compressing the middle portion of the expandable stent includes positioning the middle portion of the expandable stent within a passage extending through a collapsing fixture with the first end portion positioned outside of the passage.

3. The method of claim 2, wherein the collapsing fixture has an open configuration and a closed configuration.

4. The method of claim 3, wherein the collapsing fixture includes an outer ring and a plurality of movable elements operatively connected thereto, the plurality of movable elements being configured to move radially inward relative to the outer ring to radially compress the expandable stent in the closed configuration.

5. The method of claim 4, wherein each of the plurality of movable elements includes a rolling element proximate the outer ring in the open configuration.

6. The method of claim 5, wherein each rolling element includes a concave profile configured to contact the expandable stent in the closed configuration.

7. The method of claim 6, wherein when the expandable stent is disposed within the collapsing fixture in the open configuration, each rolling element is spaced apart from the expandable stent.

8. The method of claim 3, wherein the collapsing fixture includes:
   a first block portion configured to engage a second block portion in the closed configuration, the first block portion and the second block portion cooperating to at least partially define the passage; and
   a clamping portion configured to retain the first block portion in engagement with the second block portion when the collapsing fixture is in the closed configuration.

9. The method of claim 8, wherein the first block portion and the second block portion each include a tapered portion and a channel portion in communication with the tapered portion;
   wherein the channel portion of the first block portion cooperates with the channel portion of the second block portion to form a reduced diameter portion of the passage configured to radially compress a portion of the expandable stent disposed therein.

10. The method of claim 9, wherein positioning the middle portion of the expandable stent within the passage includes positioning the middle portion of the expandable stent in the channel portion of the first block portion and then engaging the second block portion with the first block portion.

11. The method of claim 3, wherein the collapsing fixture includes an annular collar at least partially defining the passage, the annular collar including a sleeve portion attached thereto;
   wherein the sleeve portion is extendable from the annular collar toward the first end of the expandable stent after positioning the middle portion of the expandable stent within the passage to radially collapse the expandable stent into the constrained configuration from the middle portion toward the first end.

12. The method of claim 11, wherein the sleeve portion includes an enlarged end opposite the annular collar, the enlarged end being configured to accept the distal end of the elongate outer sheath therein.

13. The method of claim 11, wherein the sleeve portion is a rolled material and radially compressing the expandable stent from the middle portion toward the first end of the expandable stent includes unrolling the sleeve portion toward the first end.

14. The method of claim 11, wherein the annular collar further includes a second sleeve portion attached thereto, the second sleeve portion being extendable from the annular collar toward a second end of the expandable stent opposite the first end after positioning the middle portion of the expandable stent within the passage to radially collapse the expandable stent into the constrained configuration from the middle portion toward the second end.

15. The method of claim 3, wherein positioning the middle portion of the expandable stent in the collapsing fixture occurs when the collapsing fixture is in the open configuration.

16. The method of claim 1, wherein the delivery device includes an inner shaft slidably disposed within the elongate outer sheath, and the inner shaft is disposed through a lumen of the expandable stent before the middle portion of the expandable stent is radially compressed.

* * * * *